US00PP11788P2

(12) United States Plant Patent
Roberts

(10) Patent No.: US PP11,788 P2
(45) Date of Patent: Feb. 27, 2001

(54) MINT PLANT 'CASCADE MITCHAM'

(76) Inventor: Donald D. Roberts, 630 32nd St., Corvallis, OR (US) 97330

( * ) Notice: Under 35 U.S.C. 154(b), the term of this patent shall be extended for 0 days.

(21) Appl. No.: 08/846,703

(22) Filed: Apr. 30, 1997

(51) Int. Cl.[7] ..... A01H 5/00
(52) U.S. Cl. ..... Plt./100
(58) Field of Search ..... Plt./100

(56) References Cited

PUBLICATIONS

"Induced Mutations Against Plant Diseases"; C.E. Horner, H.A. Melouk, et al; IAEA–SM–214/20; 1977.
Effect of Irradiation Upon the Essential Oil Content of Peppermint (*Mentha piperta L.*) and It's Composition; Ala Sadowska, Institute of Genetics & Plant Breeding, Warsaw Agricultural Univ. (pp. 115–118).
"The Genetic Basis for the Conversion of Menthone to Menthol in Japanese Mint"; Merritt J. Murray; Genetics, vol. 45, No. 7, Jul., 1960.
"Inter–Subgeneric Hybrids in the Genus Mentha"; Merritt J. Murray, et al; Journal of Heredity, vol. 62, No. 6, Nov.–Dec., 1971.
"Biotransformation of Monoterpenes by Mentha Cell lines: Conversion of Pulegone to Isomenthone"; D. Aviv and E. Galun; 1978, vol. 33, pp. 70–77—Journal of Medicinal Plant Research.

*Primary Examiner*—James R. Feyrer

(57) ABSTRACT

Selection M0107-4 is a new *Mentha piperita* plant that has more resistance to Verticillium wilt and mint rust than existing peppermint varieties. The essential oil produced by this plant resembles typical peppermint oil in component composition, but differs in the typical ratio of components. The oil is milder than typical peppermint oil organoleptically because it has a lower Menthol and higher Menthone content. The plant starts growth early in the spring, has vigorous growth until flowering and matures later than Mitcham type peppermint.

3 Drawing Sheets

TYPE OF PLANT AND NAME OF VARIETY

The present invention relates to a new and distinct variety of peppermint plant of the species botanically know as *Mentha piperita L.* I have named my new variety "Cascade Mitcham."

DISCOVERY AND ASEXUAL REPRODUCTION

This new peppermint was developed in a mint breeding program in which the primary objective was to develop a Mitcham type peppermint variety having acceptable oil quality and increased resistance to mint wilt caused by the soil-borne fungus, *Verticillium dahliae*. The new plant was discovered in a cultivated area on land near Albany, Oreg., and was initially identified as 84-M0107-4.

Selection 84-M0107-4 originated as a seedling from a polycross where M0107, a polyploid Mitcham peppermint plant, was the female parent. Polyploid male parents served as the pollen donors. MIRC M0107 is a seed fertile peppermint plant donated by the A.M. Todd Company of Kalamazoo, Mich., to the Mint Industry Research Council (MIRC) for a mint breeding program. Dr. M.J. Murray of the A.M. Todd Co. developed M0107, an unselfed polyploid peppermint strain of his selection 71-257 and later identified as selection 58. Selection 58 is a mutant created by irradiating Black Mitcham peppermint stolons and was released in 1972 as Todd's Mitcham peppermint.

Asexual reproduction of 84-M0107-4 was conducted each year under my direction since 1984 at a research farm and greenhouses near Albany, Oreg. Asexual reproduction has been conducted by rooting stem cuttings and by planting stolons taken from field grown plants. Characteristics of 84-M0107-4 come true to form and are established and transmitted through vegetative propagation.

BRIEF DESCRIPTION OF THE PHOTOGRAPHS

The accompanying color photographs show typical, greenhouse grown specimens of the vegetative growth of my new mint plant and depict the color as nearly true as is reasonably possible.

Photograph 1 illustrates the flowering pattern and multiple shoots of my new mint plant in accordance with the present invention.

Photograph 2 illustrates the inflorescence of my new mint plant in accordance with the present invention.

Photograph 3 illustrates mature and immature leaves of my new mint plant in accordance with the present invention. The leaf closest the ruler is a mature leaf collected from the lower main stem. The leaf in the middle is an immature leaf collected from the mid-main stem. The leaf on the right is a more ovate, smaller leaf collected from a secondary branch.

DESCRIPTION OF PLANT

My new mint plant improves upon and is distinct from other mint plants in several characteristics, including but not limited to, the following:

1. The ability to produce more oil than 'Black Mitcham' peppermint, parental genotype to the new plant and a commercial variety extensively grown;
2. A more extensive branching pattern than its parents;
3. A more vigorous growth that begins earlier in the spring than its parent;
4. Later maturity than Black Mitcham peppermint;
5. A higher level of resistance to mint wilt (*V. dahliae*) than its parent;
6. Resistance to mint rust caused by *Puccinia mentha;*

7. The ability to produce an oil that possesses a milder peppermint flavor due to a lower menthol and higher menthone content than its parent.

The performance of 84-M0107-4 in vigor and disease resistance compared to Black Mitcham is presented in Table I. Data were collected for mint wilt, rust and vigor from plants growing in our research plots from 1985 to 1989. The soil of these plots was infested with *V. dahliae*. A rating scale of 1 to 5 was used to identify the severity of disease development and indicates how vigorous the plant grew. For disease ratings, 1 indicates no disease symptoms and 5 indicates severe disease development. For vigor ratings, 1 indicates a very vigorous plant and 5 indicates a very weak, non-growing plant.

TABLE I

Performance of 84-M0107-4 over five years compared to the commercial peppermint variety Black Mitcham.

| | Verticillium Wilt | Rust | Vigor |
|---|---|---|---|
| 1985 | | | |
| M0107-4 | 1 | 2 | 1 |
| Black Mitcham | 5 | 3 | 4 |
| 1986 | | | |
| M0107-4 | 1 | 1 | 1 |
| Black Mitcham | 4 | 1 | 3 |
| 1987 | | | |
| M0107-4 | 2 | 1 | 2 |
| Black Mitcham | 4 | 1 | 4 |
| 1988 | | | |
| M0107-4 | 1 | 1 | 1 |
| Black Mitcham | 5 | 2 | 4 |
| 1989 | | | |
| M0107-4 | 1 | 1 | 1 |
| Black Mitcham | 5 | 2 | 4 |

Wilt and vigor are rated on an index from 1 to 5. 1 = no wilt and very vigorous; 5 = severe wilt and just surviving.

Black Mitcham peppermint exhibited severe wilt symptoms in each of the five years of the test with disease ratings of 4 and 5. 84-M0107-4, by comparison, exhibited mild wilt symptoms in 1987 with a rating of 2 and no wilt symptoms the other four years.

Selection 84-M0107-4 also has a high level of resistance to mint rust as shown in Table I. Rust was observed on 84-M0107-4 at a very low level in 1985 and was not present the following four years. Black Mitcham showed signs of rust three out of the five years.

Vigor was measured as growth, lack of disease, and stolon development. When compared to Black Mitcham in test plots established on wilt infected soil, 84-M0107-4 outperfomed Black Mitcham every year of the five year test. The vigor observed in the tests plots is believed to be directly related to wilt resistance. In the absence of the wilt disease, 84-M0107-4 developed strong growth, and stolons that contributed to early spring development the following year.

Early spring vigorous growth of 84-M0107-4 provides the potential for two harvests in one season. The new plant is more resistant to mint wilt (Verticillium wilt) and mint rust than Black Mitcham. Disease resistance makes the variety more suitable for producing dried leaves for teas and increases oil yield potential.

Other distinguishing characteristics of my new variety include an early start in Spring, vigorous growth and late maturity. Harvested early the plant produces an oil somewhat different than Black Mitcham peppermint with a higher l-limonene, 1,8-cineole, menthofuran, and pulegone content as shown in the 1994 and 1996 harvest data presented in Table II. When harvested later than Black Mitcham peppermint the oils are more similar (1995 harvest Table II). The mature oil of 84-M0107-4 has a somewhat lower menthol and higher menthone and pulegone content than Black Mitcham peppermint. Organoleptically the oil has the properties of peppermint oil. The lower l-menthol content of the new mint variety provides a milder peppermint flavor while retaining the typical peppermint organoleptic properties.

TABLE II

Composition of 84-M0107-4 Peppermint Oil from Test Plots Compared to Typical Black Mitcham Peppermint Oil.

| | 84-M0107-4 Harvest Date | | | Black Mitcham |
|---|---|---|---|---|
| Component | July 1994 | Aug. 1996 | Sept. 1995 | 1995 |
| α-Pinene | 0.62 | 0.66 | 0.48 | 0.77 |
| β-Pinene | 0.89 | 0.95 | 0.75 | 0.96 |
| l-Limonene | 2.60 | 1.89 | 1.82 | 1.37 |
| 1,8-Cineole | 4.21 | 5.96 | 4.76 | 4.84 |
| 3-Octanol | 0.66 | 1.07 | 0.89 | 0.30 |
| trans-Sabinene Hydrate | 0.72 | 0.36 | 0.48 | 0.75 |
| l-Menthone | 20.28 | 43.10 | 26.24 | 23.17 |
| isoMenthone | 2.84 | 0.52 | 4.24 | 3.09 |
| Menthofuran | 5.55 | 5.82 | 1.81 | 1.55 |
| l-Menthol | 30.05 | 22.54 | 38.02 | 41.08 |
| neoMenthol | 3.42 | 3.34 | 3.43 | 3.50 |
| l-Menthyl Acetate | 8.20 | 0.93 | 3.69 | 4.69 |
| Pulegone | 6.21 | 1.86 | 3.73 | 1.30 |
| β-Caryophyllene | 2.14 | 2.11 | 1.68 | 1.94 |
| Germacrene-D | 2.18 | 1.52 | 1.20 | 1.87 |

The numbers listed in the above table are percentages based upon the analysis of the respective mint oils by gas chromatography. The percentages are determined by calculation of the relative peak areas.

Taxonomic Description of 84-M0107-4

Selection M0107-4, under field conditions in the central Willamette Valley of Oregon, is an upright bush type plant with lateral branches at each node of the main stem. The height of 84-M0107-4 will vary based on fertilizer, soil quality and water application, amongst other known factors that effect plant growth patterns. The height of 84-M0107-4 is generally equivalent to that of Black Mitcham when grown under similar conditions. Secondary and tertiary branching occurs to form a compact growth habit. For a mature plant, i.e., a plant in condition for harvest, the main stem at mid-plant (approximately between the eleventh and twelth node) is 3–5 mm in width, while the secondary branch stems and the tertiary branch stems are 2–3 mm and 1–2 mm in width, respectively.

Mature leaves at the bottom of the plant are ovate lanceolate, while leaves on secondary branch stems and immature upper leaves are more ovate. Mid-main stem leaf size at flowering is 25–30 mm in width and 50–60 mm in length. Leaf size on secondary branches at flowering is 20–25 mm in width and 20–30 mm in length. Leaf petioles on mid-main stem leaves are 5–8 mm in length while petioles on secondary branch stem leaves are 3–4 mm. Leaves on the main stem are acuminate while leaves on secondary branch stems tend to be more acute and more dentate near their tips. All leaves are more irregularly dentate than Black Mitcham peppermint. The main stem leaves have from 10 to 13 teeth on each side while secondary branch stem leaves have from 8–10 teeth on each side. The leaf is dark green in color, ranging from Royal Horticultural Society Color Code 137 A to 137 C. Leaf venation is pinnate with the main vein being reddish-purple in color from anthocynin pigment development. Veins are prominent in all leaves. Under field conditions the leaf blade curves upward at a slight angle from the main vein.

The inflorescence of 84-M0107-4 varies somewhat in shape and color. The terminal flower is a cylindrical capitate spike, while flowers on lateral branches have a more cylindrical spike shape. The cylindrical spikes are about 25 mm in diameter and 75 mm in length. The capitate flowers are about 25 mm in width and 40 mm in length. The flowers consist of five petals fused into a two-lipped corolla. The corolla is light in color, ranging from Royal Horticulture Society Color Code 75 B to 75 D, and may develop darker lavender colored markings. The calyx is generally green in color, but with some purple coloration from anthocyanin development. The sepals have rows of golden colored glands. The gynoecium consists of a single pistil with a two lobed stigma that is exserted.

The androecium consists of four stamen each with a distinct (i.e., not fused at corolla) filament and anther. The anthers are exserted.

While the plant that comprises the present invention has been described in connection with a specific embodiment thereof, it will be understood that this application is intended to cover any variations, uses, or adaptations of the invention (particularly those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improved resistance to mint wilt and rust, vigorous growth and a milder tasting oil.

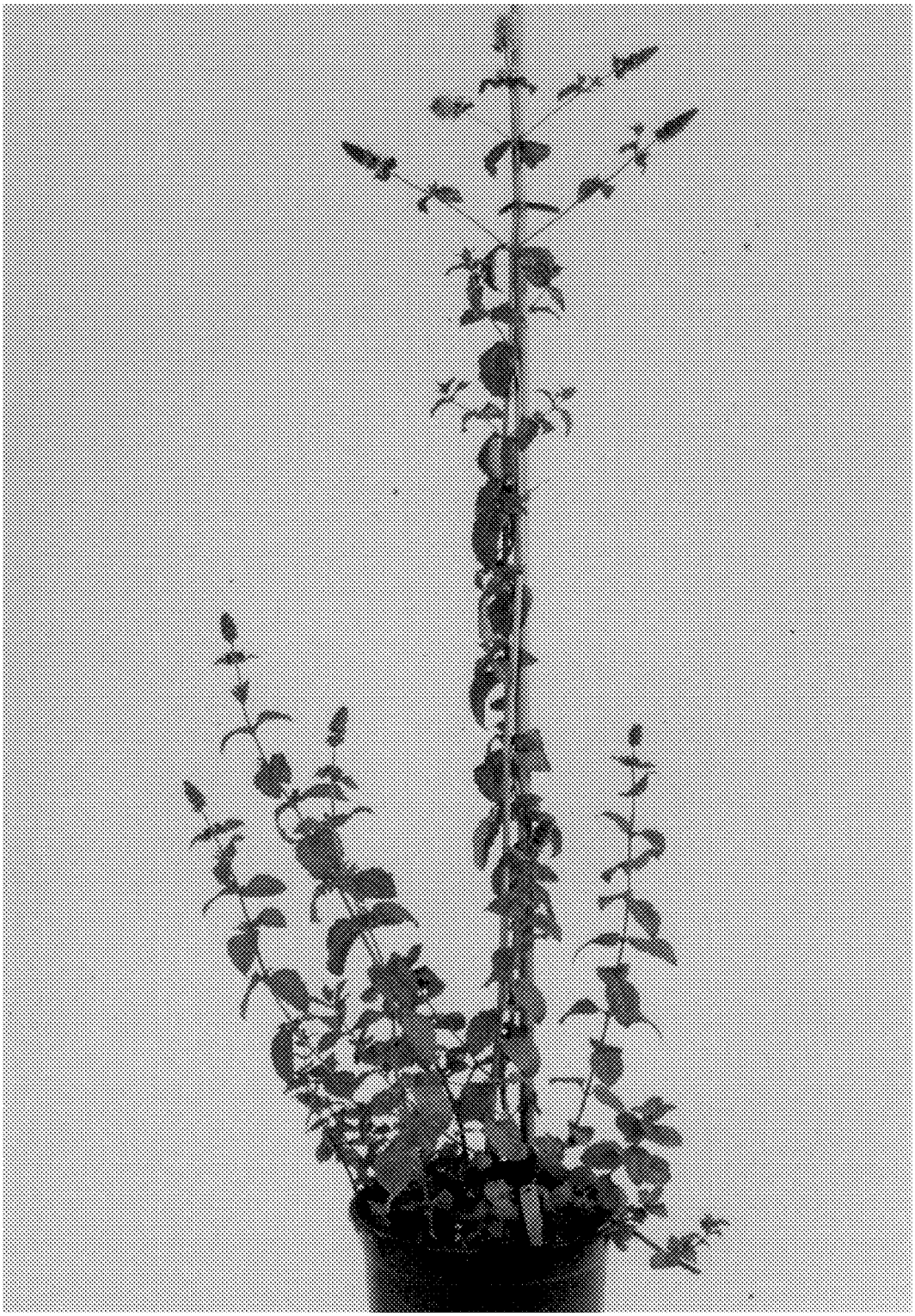

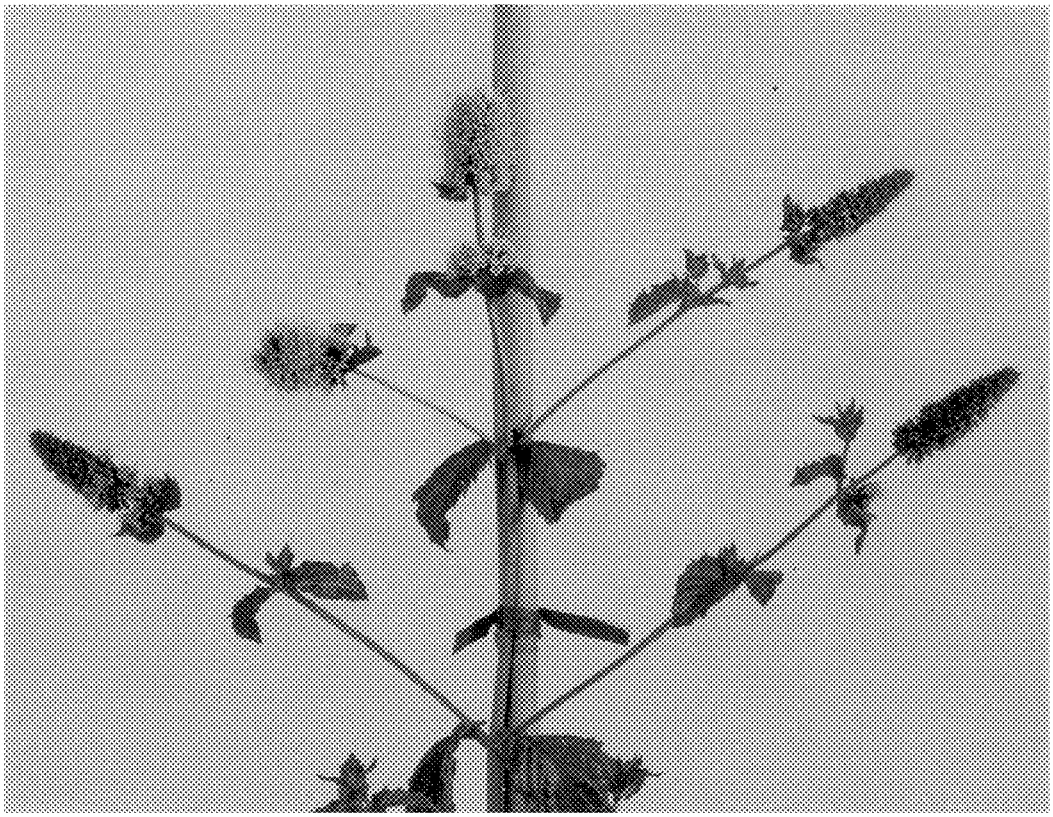

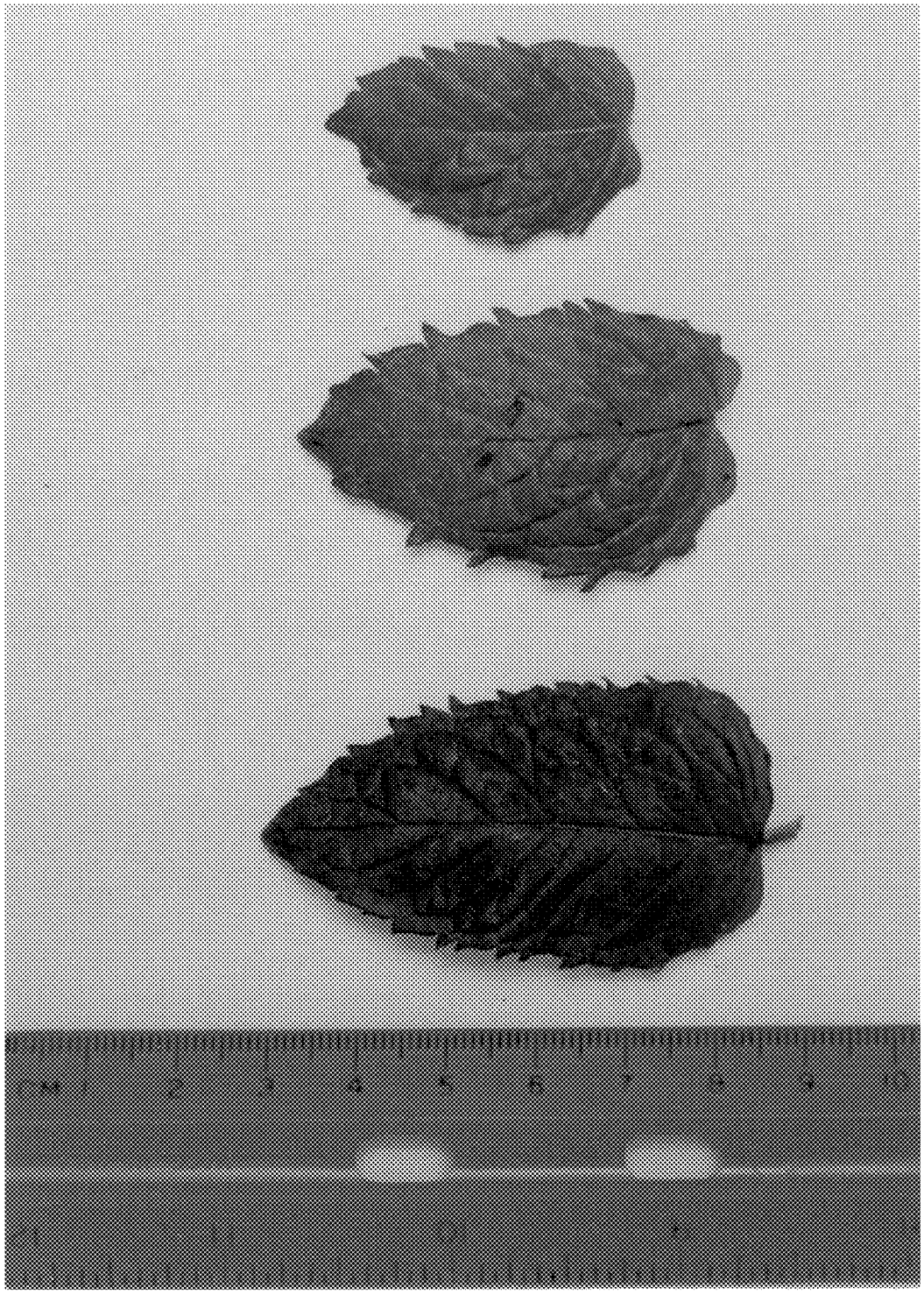

* * * * *